United States Patent [19]

Ishikawa

[11] Patent Number: 4,731,889
[45] Date of Patent: Mar. 22, 1988

[54] SAFETY LATCH FOR A TILTING BED

[75] Inventor: Naobumi Ishikawa, Ootawara, Japan

[73] Assignee: Kabushiki Kaisha Toshiba, Kawasaki, Japan

[21] Appl. No.: 832,877

[22] Filed: Feb. 26, 1986

[30] Foreign Application Priority Data

Feb. 27, 1985 [JP] Japan .................... 60-38061

[51] Int. Cl.⁴ .................... A61B 6/04; A61G 13/00
[52] U.S. Cl. .................... 5/62; 5/424; 5/509; 269/323; 378/179; 378/209
[58] Field of Search .................... 5/62, 61, 60, 167, 509, 5/424, 108, 109; 269/323, 325, 326; 378/209, 177, 179, 195, 196; 74/527, 530

[56] References Cited

U.S. PATENT DOCUMENTS

| | | | |
|---|---|---|---|
| 1,299,894 | 4/1919 | Anderson | 269/323 |
| 2,508,449 | 5/1950 | Davis, Jr. et al. | 378/196 |
| 2,680,046 | 6/1954 | Stava | 378/209 |
| 2,692,173 | 10/1954 | Lowitzsch | 378/209 |
| 3,396,274 | 8/1968 | Hogan | 378/209 |
| 3,473,024 | 10/1969 | Feiertag | 378/209 |
| 3,805,080 | 4/1974 | Yager et al. | 269/323 |
| 3,831,032 | 8/1974 | Putod | 378/196 |
| 4,164,656 | 8/1979 | Krasznai et al. | 378/209 |
| 4,452,439 | 6/1984 | Hogan | |

FOREIGN PATENT DOCUMENTS

| | | | |
|---|---|---|---|
| 1466926 | 5/1969 | Fed. Rep. of Germany | 378/179 |
| 2932755 | 3/1981 | Fed. Rep. of Germany | 378/209 |
| 2940381 | 4/1981 | Fed. Rep. of Germany | 378/209 |
| 382665 | 2/1908 | France | 269/325 |

Primary Examiner—Alexander Grosz
Assistant Examiner—Carl M. DeFranco, Jr.
Attorney, Agent, or Firm—Finnegan, Henderson, Farabow, Garrett & Dunner

[57] ABSTRACT

This invention provides a highly reliable safety device having a high fail-safe feature, which comprises a sector gear rotatably supported on a support base, a bed section supported on the sector gear and tiltable to a predetermined diagnostic angle anywhere from a horizontal position to a standing position of a patient, an off-normal rotation control means such as a limit switch to detect that the rotation of the sector gear relative to the support base exceeds the range of a limit rotation angle and to control its rotation, a hook member provided in a side surface position of the sector gear corresponding to the limit rotation angle beyond the off-normal rotation angle, a hook holding mechanism journaled in a side surface position of said support base which faces the sector gear, and adapted to engage with the hook member to restrict and prevent any further rotation of the sector gear, and whereby the bed section is positively restricted against any further tilting beyond its limit rotation angle, immediately informing an operator of an off-normal state of the safety device, preventing a possible accident on the bed section and the patient.

7 Claims, 12 Drawing Figures ures 4,731,889

SAFETY LATCH FOR A TILTING BED

BACKGROUND OF THE INVENTION

This invention relates to a safety device for a tilting bed of an X-ray diagnostic apparatus etc., which prevents a rotation of a bed beyond a limit rotation angle.

A tilting bed for an X-ray diagnostic apparatus etc., is so constructed that it is tiltable to permit a human subject (patient) to be held at a desired diagnostic angle anywhere from a horizontal position to a standing position. A safety device is provided on the tilting bed to prevent a rotation of the latter beyond a predetermined tilting angle. FIGS. 6A and 6B show one example of a conventional tilting bed device for X-ray diagnostic apparatuses which is equipped with the aforementioned safety device. FIGS. 7A and 7B are an enlarged view showing portions A and B in FIG. 6A, i.e., major parts of the aforementioned safety device.

That is, tilting bed device 1 shown in FIGS. 6A and 6B includes bed section 2, support base 3 for supporting the bed section, sector gear 4 of a semicircular configuration, and rotation shaft 5 fixed to the sector gear. One end of shaft 5 is rotatably supported on support base 3. To the other end of shaft 5 is rotatably attached a pinion gear 9 which is in mesh with a guide rail rack for the aforementioned bed section 2. Gear grooves 4a are provided on the outer periphery of the sector gear 4 and are in mesh with drive gear 8 provided on the inside surface of the support base 3.

A chord section defined at the upper edge of sector gear 4 faces upwardly on a top plate side of bed section 2 and a pair of cam followers 6, 6 are located inwardly in the neighborhood of the chord section of sector gear 4 in a spaced-apart relation and are projected in a direction of bed section 2. Guide rail 7 is mounted on the bed section side and has rail groove 7a of a U-shaped configuration formed, on the top plate side, along the longitudinal direction of the bed section with cam follower 6 kept in engagement with rail groove 7a. Pinion gear 9 on rotation shaft 5 engages with rack 7b located on the lower surface of guide rail 7. A drive motor, not shown, is connected to drive gear 8. When drive gear 8 is driven in a direction of, for example, arrow $a_1$ in FIG. 6A, the sector gear in mesh with drive gear 8 is rotated in a direction of arrow $a_2$ with rotation shaft 5 as a center to permit bed section 2 to be tilted in accordance with its rotation angle. Pinion gear 9 is coupled through a transmission, not shown, to the motor for drive gear 8. The rotation in a direction of arrow $b_1$ of pinion gear 9 causes guide rail 7 to be moved, in a direction of arrow $b_2$, through a rack $7_b$ which engages with pinion gear 9. Thus, bed section 2 can be tilted at a desired rotation angle anywhere from the horizontal position to the standing position of the patient. Furthermore, since the bed section is raised in the tilting direction during the rotation of the pinion gear, there is no possibility that the bed section will come into contact with a floor.

The raising of bed section 2 in the tilting bed is achieved by the longitudinal movement of guide rail 7 which engages with cam follower 6. Where an excess rise of the bed section, such as a state of the disengagement of the bed section from guide rail 7, takes place, the bed section is removed away from the support base, causing an accident to occur on the patient. As a countermeasure against a possible accident, a safe provision is made for the conventional device with restriction placed on the angle through which the bed section is tilted, thereby preventing rotation of a bed beyond that tilting angle. In this connection, a first safe measure is adopted which comprises setting a limit rotation angle beyond a normal tilting range relative to the rotation of the sector gear, locating a limit switch actuating piece in proper place relative to the surface position of the sector gear corresponding to the limit rotation angle, and actuating the limit switch, upon the rotation of gear 4 to an extent corresponding to the limit rotation angle, interrupting a power supply to the motor and thus preventing further rotation of the sector gear. Second and third safe measures as set out below can also be adopted according to this invention. That is, a stopper is provided as a mechanical means as shown, for example, in FIGS. 7A and 7B. In the arrangement shown in FIG. 7A, a metal piece 4b is deposited by, for example, welding onto the groove of the last gear tooth of a gear train of the sector gear, that is, at a location past the limit rotation angle position where the aforementioned limit switch actuating piece is placed. In the arrangement shown in FIG. 7B a blocklike stopper 7c is fitted into the rail groove of guide rail 7, preventing the detachment of the cam follower from the rail groove.

The aforementioned stopper prevents sector gear 4 and guide rail 7 from being rotated and moved, respectively, beyond their limit range. Since an inertial force acts upon the bed section on which the weight of the patient has been heavily inflicted, there is a greater risk that the stopper will be destroyed due to the collision of drive gear 8 or cam follower 6 with the stopper. The stopper acts as such when bed section 2 is rotated beyond the limit rotation angle, that is, when the limit switch as a control means for an off-normal rotation of the bed section fails. In other words, the stopper serves as such when the bed section is operated without noticing any off-normal state in which the off-normal rotation control mean has been placed. The repetitive collisions of the drive gear and cam follower with the stopper due to the rotation of the bed section beyond the limit rotation angle cause a mechanical fatigue to be gradually induced in the stopper, resulting in a eventual breakage of the stopper. Since the stopper is provided as a final safety securing means for the tilting bed device, the tilting bed has a greater risk of being injured or destroyed, giving a fatal below to the bed section. Thus, there is a growing demand for a safer tilting bed device.

SUMMARY OF THE INVENTION

It is accordingly the object of this invention to provide a fail-safe feature-incorporated safety device which, when a bed section is tilted to a limit rotation angle, it is prevented against rotation and thus restricted from any subsequent movement so that the tilting operation of the bed device cannot be continued without performing additional or separated operation, positively informing an operator of an off-normal state of the safety device which is detected by an off-normal rotation control means located before the limit rotation angle position.

According to this invention there is provided a highly reliable safety device having a high fail-safe feature, which comprises:
  a sector gear rotatably supported on a support base;
  a bed section supported on the sector gear and tiltable to a predetermined diagnostic angle anywhere from a horizontal position to a standing position of a patient;

an off-normal rotation control means to detect that the rotation of the sector gear relative to the support base exceeds the range of a limit rotation angle and to control its rotation;

a hook member provided in a side surface position of the sector gear corresponding to the limit rotation angle beyond the off-normal rotation angle;

a hook holding mechanism journaled in a side surface position of said support base which faces the sector gear, and adapted to engage with the hook member to restrict and prevent any further rotation of the sector gear; and whereby the bed section is positively restricted against any further tilting beyond its limit rotation angle, immediately informing an operator of an off-normal state of the safety device, preventing a possible accident on the bed section and the patient.

DETAILED DESCRIPTION OF THE PREFERRED EMBODIMENTS

The embodiment of this invention will be explained below with reference to the accompanying drawings.

Figure 1A:
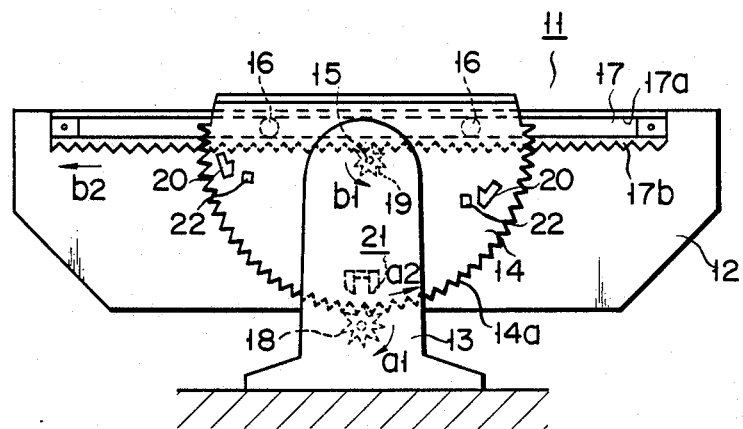
FIGS. 1A and 1B are a front view and side view showing a safety device for a tilting bed, according to one embodiment of this invention.
Figure 1B:
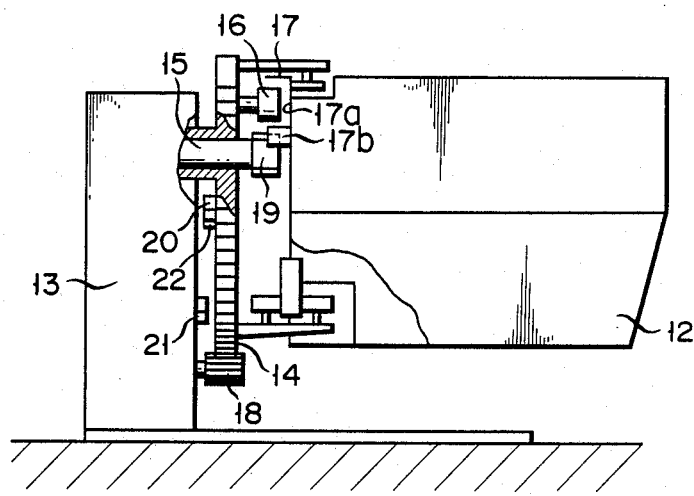

In FIGS. 1A and 1B, bed tilting device 11 includes bed section 12, support base 13 for tiltably supporting the bed section, and sector gear 14 of a semicircular configuration fixed to rotation shaft 15. One end of the rotation shaft is rotatably supported on the support base, and pinion gear 19 is rotatably mounted on the other end of the rotation shaft.

The gear grooves 14a are formed on the outer peripheral surface of sector gear 14 and engage with drive gear 18 supported on the inside surface of support base 13. A chord section defined at the upper edge of sector gear 14 faces upwardly on the top plate side of bed section 12 and a plurality of cam followers 16 are located, at a predetermined interval, inwardly in the neighborhood of the chord section of the sector gear and projected in a direction of the bed section. Guide rail 17 is mounted on the top plate side of the bed section and has a rail groove 17a of a U-shaped configuration along the longitudinal direction of the bed section with cam follower 16 kept in engagement with groove 17a. Rack 17b is provided on the lower surface of the guide rail and engages with pinion gear 19 which is rotatably mounted on the other end of rotation shaft 15. Drive gear 18 is coupled to a drive motor, not shown, for drive. The rotation of gear 18 in a direction of, for example, arrow $a_1$ in FIG. 1A causes sector gear 14 in mesh with drive gear 18 to be rotated in a direction of arrow $a_2$ with the rotation shaft as a center, permitting the bed section to be tilted to an extent corresponding to that rotation angle. Pinion gear 19 is coupled to the motor through a transmission not shown. The rotation of gear 19 in the direction of arrow $b_1$ in FIG. 1A causes guide rail 17 in mesh with pinion gear 19 to be moved in a direction of arrow $b_2$ in FIG. 1A through the rack 17b. In this way, the bed section can be tilted to a predetermined diagnostic angle anywhere from a horizontal position to a standing position of the patient through the rotation of the sector gear 14. In this case, the sector gear is moved such that the bed section is moved in the tilting direction without causing the end of the bed section to come in contact with a floor.

Figure 2:
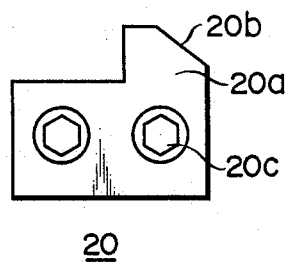
FIGS. 2 and 3 are enlarged views showing a safety mechanism which is a major portion of the safety device of FIGS. 1A and 1B.

In the structure of FIG. 1, reference numerals 20 and 21 show a hook member and hook holding mechanism, respectively. The hook member has hook portion 20a and cut area 20b on one side as shown in FIG. 2 and is fixed by bolt 20c to the inside surface of sector gear 14, with hook portion 20a facing upward, where the sector gear faces support base 13. The hook member 20 is mounted in a position corresponding to the limit rotation angle of the sector gear, that is, in a position beyond a position where limit switch 22 is provided, as an off-normal rotation control means, on the inside surface of the sector gear.

Figure 3:
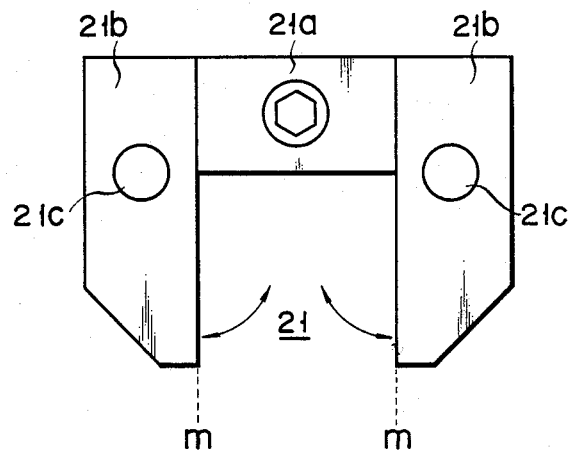

As shown in FIG. 3, hook holding mechanism 21 has block base 21a and a pair of engaging hooks 21b each mounted in abutment with the corresponding end face of block base 21a and each supported such that it is rotatable with shaft 21c, as a center. The engaging hooks 21b are arranged with the block base sandwiched therebetween to provide an inverted U-shaped configuration. The base block 21a serves as a stopper with the engaging hook rotatable not beyond a reference range m in FIG. 3, but within that reference range.

Figure 4A:
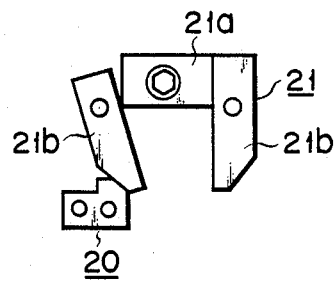
FIGS. 4A to 4C are explanatory views showing an operative state of the aforementioned safety device.
Figure 4B:
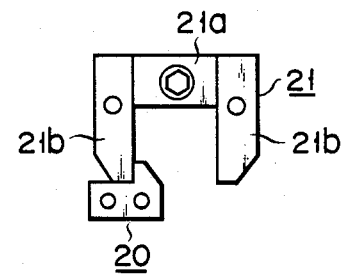
Figure 4C:
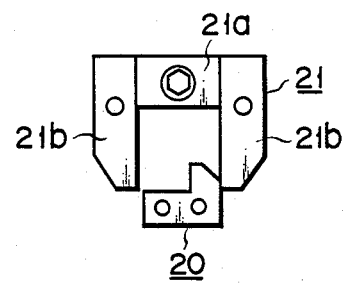

In the aforementioned safety device, the bed section is moved normally through a predetermined tilting angle by the rotation of sector gear 14. With the bed section rotated beyond that angle, the aforementioned limit switch 22 is operated, causing the tilting motion of the bed section to be stopped. With sector gear 14 rotated up to the limit rotation angle beyond the operation range of limit switch 22, hook member 20 for sector gear 14 is moved up to the position of the hook holding mechanism 21 and, as shown in FIG. 4A, hook member 20 pushes aside one engaging hook 21b of hook holding mechanism 21, enters a U-shaped spacing defined by the U-shaped hook holding mechanism and collides with the other engaging hook 21b as shown in FIG. 4C. Since said other engaging hook 21b is not rotated outwardly beyond the reference range m, any further rotation of the sector gear is stopped at that position. That engaging hook 21b which has been pushed aside by hook member 20 is returned, under its own weight, to an original position as shown in FIG. 4B. Even if in this state the sector gear 14 is reversely rotated, the hook member is moved back to the position of said one engaging hook 21b beyond which hook portion 20a is not further moved due to its engagement with said one engaging hook 21b. As a result, the bed section is restricted at that position. This restricted position is held unless the hook member 20 is disengaged from the hook holding mechanism 21.

If in this way the safety device is in an operative state, the bed section is kept at a locked state, preventing any further tilting movement. Thus, the operator can readily and positively know a failure of, for example, the off-normal rotation control means, enabling him to take an immediate necessary action, such as repair. Therefore, there is no possibility that any repetitive operation of the safety device as the final safety means without knowledge of such a state will be done and a consequent failure will occur due to a build-up of a mechanism fatigue in the device as in the conventional safety device. This offers a more reliable safety device having a high fail-safe feature.

Figure 5:
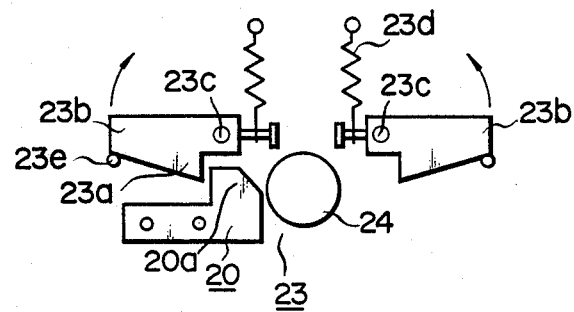
FIG. 5 is an expanded front view showing a safety device according to another embodiment of this invention.
Figure 6A:
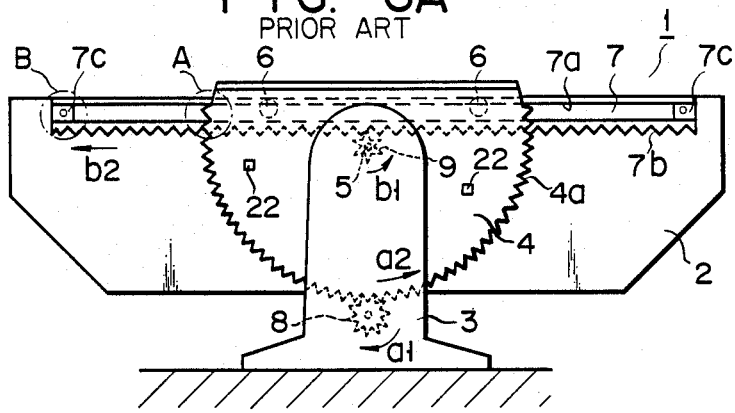
FIGS. 6A and 6B are a front view and side view, respectively, showing a conventional safety device for a tilting bed.
Figure 6B:
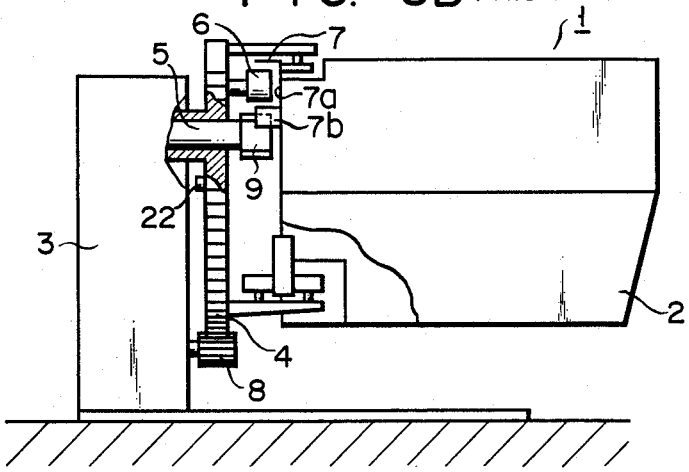
Figure 7A:
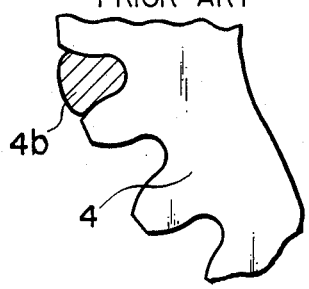
FIGS. 7A and 7B are expanded, partial front views showing a safety mechanism of a conventional bed tilting device.
Figure 7B:
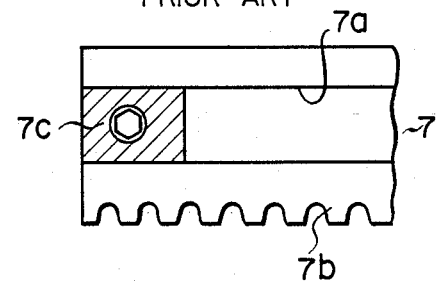

This invention is not restricted to the aforementioned embodiment. A variety of changes or modifications may be made without departing from the spirit and scope of this invention. For example, hook holding mechanism 21 shown in FIG. 3 may be changed as shown in FIG. 5. Hook holding mechanism 23 comprises stopper 24 fixed to support base 13 and a pair of engaging hooks 23b, 23b located, with stopper 24 placed therebetween, and rotatably supported each through a shaft 23c projected from support base 13. The hook holding mechanism 23 has engaging hook portion 23a engageable with hook portion 20a of hook member 20. Engaging hooks 23b are each attached, at one end, to support base 13 through spring 23d and each engage, at the other end portion, with stopper pin 23e to permit engagement hook 23b to be rotated only in a direction of an arrow in FIG. 5 with shaft 23c as a fulcrum. In the aforementioned arrangement, counterclockwise rotation of sector gear 14 causes hook member 20 to move to the right as seen in FIG. 9; and push aside engaging hook portion 23a of engaging hook 23b, and come into abutting engagement with stopper 24. Then, the engaging hook portion 23a of the spring -biased engaging hook 23b engages with hook portion 20a of hook member 20 to restrict movement of hook member 20 to the left. As a result, the rotation of sector gear 14 can be restricted in its limit rotation angle position, thus obtaining the same advantage as set out above. Although the safety device of this invention has been described in connection with its advantage, a stopper mechanism as shown in FIG. 7 may also be added to the safety device.

What is claimed is:

1. A tilting bed, comprising:
   a. a support base having a mounting surface portion;
   b. a sector gear rotatably supported on said support base and having a side surface facing said mounting surface portion of said support base;
   c. a bed section supported on said sector gear and selectively tiltable to a desired diagnostic position by rotation of said sector gear to a desired rotation angle relative to said supoprt base, said desired rotation angle being within a preselected normal rotation angle range;
   d. drive means for rotating said sector gear;
   e. off-normal rotation control means for stopping operation of said drive means when said sector gear is rotated to a preselected off-normal angle, said off-normal rotation angle being beyond said normal rotation angle range by a preselected first marginal angle; and
   f. safety stop means for holding said sector gear when said sector gear is rotated to a preselected limit angle, said limit angle being beyond said normal rotation angle range by a preselected second marginal angle greater than said first marginal angle, said safety stop means including:
   a hook member mounted on said side surface of said sector gear and having a hook portion, and
   hook holding means for engaging said hook member and holding said sector gear when said sector gear is rotated beyond said normal rotation angle range to said limit angle, said hook holding means including a pair of engaging hooks mounted on said mounting surface portion of said support base in a spaced-apart relation and rotatable only inwardly toward each other, whereby, when said sector gear is rotated beyond said normal rotation angle range and said off-normal rotation angle to said limit angle, said hook member pushes aside one of said engaging hooks to cause said one of said engaging hooks to be inwardly rotated toward the other of said engaging hooks, and then said hook member is positioned and held between said engaging hooks.

2. The tilting bed according to claim 1, wherein said off-normal rotation control means includes a limit switch mounted on said side surface of said sector gear.

3. The tilting bed according to claim 2, wherein said limit switch is mounted on said side surface of said sector gear at a position proximate said hook holding means when said sector gear is at said off-normal rotation angle.

4. A tilting bed, comprising:
   a. a support base having a mounting surface portion;
   b. a sector gear rotatably supported on said support base and having a side surface facing said mounting surface portion of said support base;
   c. a bed section supported on said sector gear and selectively tiltable to a desired diagnostic position by rotation of said sector gear to a desired rotation angle relative to said support base, said desired rotation angle being within a preselected normal rotation angle range;
   d. drive means for rotating said sector gear;
   e. off-normal rotation control means for stopping operation of said drive means when said sector gear is rotated to a preselected off-normal rotation angle, said off-normal rotation angle being beyond said normal rotation angle range by a preselected first marginal angle; and
   f. safety stop means for holding said sector gear when said sector gear is rotated to a preselected limit angle, said limit angle being beyond said normal rotation angle range by a preselected second marginal angle greater than said first marginal angle, said safety stop means including:
   a hook member mounted on said side surface of said sector gear, and
   hook holding means for engaging said hook member and holding said sector gear when said sector gear is rotated beyond said normal rotation angle range to said limit angle, said hook holding means including a pair of engaging hooks pivotally mounted on said mounting surface portion of said support base in a spaced-apart relation and a stopper fixed to said mounting surface portion of said support base between said engaging hooks, each of said engaging hooks being rotatable only in one direction, whereby, when said sector gear rotates beyond said normal rotation angle range and said off-normal angle to said limit angle, said hook member pushes aside one of said engaging hooks to cause said one of said engaging hooks to be rotated in said one direction, and then said hook member is positioned and held between said one engaging hook and said stopper.

5. The tilting bed according to claim 4, wherein said hook holding means includes a pair of springs, each of said springs having one end attached to one of said engaging hooks and resisting rotation of said one engaging hook in said one direction.

6. The tilting bed according to claim 4, wherein said off-normal rotation control means includes a limit switch mounted on said side surface of said sector gear.

7. The tilting bed according to claim 6, wherein said limit switch is mounted on said side surface of said sector gear at a position proximate said hook holding means when said sector gear is at said off-normal rotation angle.

* * * * *

UNITED STATES PATENT AND TRADEMARK OFFICE
CERTIFICATE OF CORRECTION

PATENT NO.   :   4,731,889
DATED        :   March 22, 1988
INVENTOR(S)  :   Naobumi Ishikawa It is certified that error appears in the above-identified patent and that said Letters Patent is hereby corrected as shown below:

Claim 1, column 5, line 51, change "supoprt" to --support--.

Signed and Sealed this

Twenty-seventh Day of September, 1988

*Attest:*

DONALD J. QUIGG

*Attesting Officer*           *Commissioner of Patents and Trademarks*